US012582838B2

(12) United States Patent
Hanania et al.

(10) Patent No.: US 12,582,838 B2
(45) Date of Patent: Mar. 24, 2026

(54) UNIVERSALLY FRIENDLY OBTURATOR (UFO) FOR BRACHYTHERAPY TREATMENT OF CERVICAL CANCER

(71) Applicants: Baylor College of Medicine, Houston, TX (US); William Marsh Rice University, Houston, TX (US)

(72) Inventors: Alexander Hanania, Houston, TX (US); Michelle S. Ludwig, Houston, TX (US); Elisa Arango, Bellaire, TX (US); Susannah Dittmar, Menlo Park, CA (US); Krithika Kumar, Houston, TX (US); Lauren Payne, McKinney, TX (US); Sanika Rane, Houston, TX (US); Andrea Samantha Gobin, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 17/644,124

(22) Filed: Dec. 14, 2021

(65) Prior Publication Data

US 2022/0184417 A1      Jun. 16, 2022

Related U.S. Application Data

(60) Provisional application No. 63/125,546, filed on Dec. 15, 2020.

(51) Int. Cl.
*A61N 5/10*              (2006.01)
(52) U.S. Cl.
CPC ......... *A61N 5/1016* (2013.01); *A61N 5/1027* (2013.01); *A61N 2005/1009* (2013.01)

(58) Field of Classification Search
CPC .... A61N 2005/1008; A61N 2005/1024; A61N 2005/1025; A61N 5/1007; A61N 5/1002
See application file for complete search history.

(56) References Cited

U.S. PATENT DOCUMENTS

| | | | | |
|---|---|---|---|---|
| 6,238,332 B1 * | 5/2001 | Kanesaka | ............ | A61N 5/1002 |
| | | | | 600/3 |
| 7,666,130 B2 | 2/2010 | Mick | | |
| 9,737,729 B2 | 8/2017 | Van Erp et al. | | |
| | | (Continued) | | |

FOREIGN PATENT DOCUMENTS

| | | | |
|---|---|---|---|
| WO | 2015023307 A1 | 2/2015 | |

*Primary Examiner* — Samuel G Gilbert
(74) *Attorney, Agent, or Firm* — Saul Ewing LLP; Kathryn Doyle; Sean P. Ritchie

(57) ABSTRACT

The present invention provides a brachytherapy applicator device having: an elongate body defining a plurality of brachytherapy needle channels, each adapted and configured to receive a brachytherapy needle; a proximal end defining a plurality of proximal openings, each in communication with one of the plurality of brachytherapy needle channels; and a distal end defining a plurality of distal openings, each in communication with one of the plurality of brachytherapy needle channels, wherein at least some of the plurality of brachytherapy needle channels are curved away from a central axis of the elongate body at the distal end such that a brachytherapy needle inserted therethrough will engage with tissue lateral to a cross-sectional profile of the distal end of the elongate body.

14 Claims, 9 Drawing Sheets

(56) References Cited

U.S. PATENT DOCUMENTS

2007/0270627 A1* 11/2007 Cutrer .................. A61N 5/1015
                                                    600/7
2020/0016428 A1* 1/2020 Verhaegen ........... A61N 5/1002

* cited by examiner

110

9 cm 35 cm

UNIVERSALLY FRIENDLY OBTURATOR (UFO) FOR BRACHYTHERAPY TREATMENT OF CERVICAL CANCER

CROSS-REFERENCE TO RELATED APPLICATION

This application claims the benefit of priority under 35 U.S.C. § 119(e) to U.S. Provisional Patent Application Ser. No. 63/125,546, filed Dec. 15, 2020. The entire content of this application is hereby incorporated by reference.

BACKGROUND OF THE INVENTION

Brachytherapy (BT) is a cancer treatment involving the placement of a sealed, high-dose radiation source at or near the site of the tumor and is the only curative treatment for late-stage and/or locally advanced cervical cancer, inoperable endometrial cancer, and vaginal apex cancer.

SUMMARY OF THE INVENTION

One aspect of the invention provides a brachytherapy applicator device including: an elongate body defining a plurality of brachytherapy needle channels, each adapted and configured to receive a brachytherapy needle; a proximal end defining a plurality of proximal openings, each in communication with one of the plurality of brachytherapy needle channels; and a distal end defining a plurality of distal openings, each in communication with one of the plurality of brachytherapy needle channels. At least some of the plurality of brachytherapy needle channels are curved away from a central axis of the elongate body at the distal end such that a brachytherapy needle inserted therethrough will engage with tissue lateral to a cross-sectional profile of the distal end of the elongate body.

This aspect of the invention can have a variety of embodiments. The applicator can include a central channel adapted and configured for receiving one or more selected from a tandem device and a brachytherapy needle.

The plurality of brachytherapy needle channels can include one or more selected from: from about 30 channels to about 35 channels, from about 35 channels to about 40 channels, from about 40 channels to about 45 channels, and from about 45 channels to about 50 channels.

The applicator can further include an external afterloader adapted and configured to introduce one or more radiation doses into the plurality of channels.

At least some of the plurality of brachytherapy needle channels can be curved away from a central axis of the elongate body at the proximal end.

The plurality of brachytherapy needle channels can be evenly spaced along concentric radii of the cross-section of the applicator. The cross-sectional profile of the proximal end of the elongate body can include a stepped surface, wherein the proximal openings positioned along the outermost concentric radii protrude further than proximal openings positioned along the innermost concentric radii.

The cross-sectional profile of the distal end of the elongate body can include a smooth surface with one or more indentations adapted and configured to complement the curvature of the cervix of a patient.

The diameter of elongate body can be between about 3.5 cm and about 6 cm.

The applicator device can have a length of about 13 cm. The central portion of the elongate body can have a length of about 9 cm.

The applicator device can have a length of about 15 cm. The central portion of the elongate body can have a length of about 11 cm.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

Figure 1:
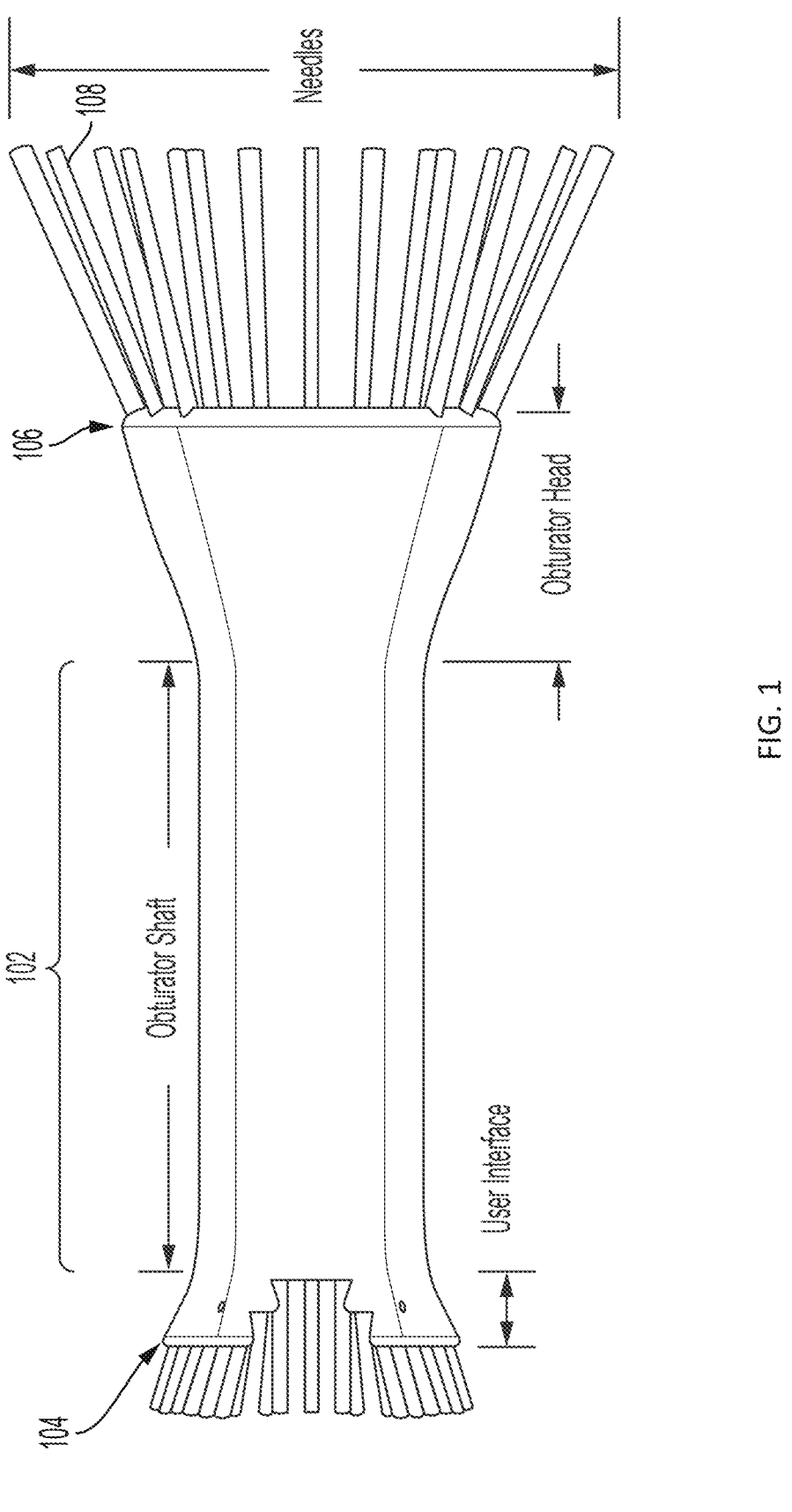
FIG. 1 depicts an exemplary Universally Friendly Obturator (UFO) of the present invention, as contemplated herein.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

The terms "proximal" and "distal" can refer to the position of a portion of a device relative to the remainder of the device or the opposing end as it appears in the drawing. The proximal end can be used to refer to the end manipulated by the user. The distal end can be used to refer to the end of the device that is inserted and advanced and is furthest away from the user. As will be appreciated by those skilled in the art, the use of proximal and distal could change in another context, e.g., the anatomical context in which proximal and distal use the patient as reference, or where the entry point is distal from the user.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

The present invention provides a universally-friendly obturator device, or UFO, for administering brachytherapy to a subject for the treatment of gynecologic cancers including, for example, cervical cancer, primary vaginal cancer, and endometrial cancer such as endometrial cancer that may otherwise be inoperable. The present invention also provides methods for administering brachytherapy to a patient for the treatment of gynecologic cancer using the brachytherapy device as described herein. The present invention allows for the administration of brachytherapy including interstitial brachytherapy without the use of transcutaneous needles.

Current methods of interstitial brachytherapy heavily rely on the use of transcutaneous interstitial needles to treat cervical cancer: up to 40 needles can be used to treat the full extent of large, locally advanced tumors. These needles are highly invasive, as their placement increases the risk of damage to vital surrounding structures. Physicians must be extremely careful when placing transcutaneous needles, so this procedure requires a high level of expertise and becomes time-intensive, taking 2-2.5 hours on average.

Elongate Body

Referring now to FIG. 1, the UFO brachytherapy applicator 100 of the present invention includes an elongate body 102 having a central axis and a plurality of brachytherapy needle channels, each adapted and configured for accommodating one or more brachytherapy needles 108. The brachytherapy applicator 100 includes a proximal end 104 having a plurality of proximal openings, each adapted and configured for receiving a brachytherapy needle, and a distal end 106 having a plurality of distal openings, each in communication with one of the brachytherapy channels passing through the elongate body.

The elongate body of the UFO brachytherapy applicator contains a plurality of brachytherapy needle channels. The plurality of channels may include up to about 20 channels, from about 20 channels to about 25 channels, from about 25 channels to about 30 channels, from about 30 channels for about 35 channels, from about 35 channels to about 40 channels, about 40 channels to about 45 channels, from about 45 channels to about 50 channels, from about 50 channels to about 55 channels, from about 55 channels to about 60 channels, from about 60 channels to about 65 channels, from about 65 channels to about 70 channels, and so on. In some embodiments, the plurality of channels includes 44 channels. In some embodiments, the plurality of channels includes about 45 channels. That is, each needle channel may engage with 1 brachytherapy needle, 2 brachytherapy needles, 3 brachytherapy needles, 4 brachytherapy needles, 5 brachytherapy needles, and so on. Embodiments of the brachytherapy needle channels can have a diameter of about 2.5 mm. The brachytherapy needle channels may have a diameter of up to about 0.1 mm, from about 0.1 mm to about 0.2 mm, from about 0.2 mm to about 0.3 mm, from about 0.3 mm to about 0.4 mm, from about 0.4 mm to about 0.5 mm, from about 0.5 mm to about 0.6 mm, from about 0.6 mm to about 0.7 mm, from about 0.7 mm to about 0.8 mm, from about 0.8 mm to about 0.9 mm, from about 0.9 mm to about 1.0 mm, from about 1.0 mm to about 1.1 mm, from about 1.1 mm to about 1.2 mm, from about 1.2 mm to about 1.3 mm, from about 1.3 mm to about 1.4 mm, from about 1.4 mm to about 1.5 mm, and any and all increments therebetween. In some embodiments, each of the channels may have the same diameter. In some embodiments, the channels may have different diameters.

Embodiments of the cross-sectional profile of the elongate body 102 can have a uniform width with flaring at the proximal end and distal end. The cross-sectional profile may have a curved shape that may complement the vaginal canal. For example, the cross-sectional shape may include a circle, an oval, and the like. The cross-sectional shape may have a maximum diameter or cross-sectional dimension of up to about 1 mm, from about 1 mm to about 1.5 mm, from about 1.5 mm to about 2 mm, from about 2 mm to about 2.5 mm, from about 2.5 mm to about 3 mm, from about 3 mm to about 3.5 mm, from about 3.5 mm to about 4 mm, from about 4 mm to about 4.5 mm, from about 4.5 mm to about 5 mm, from about 5 mm to about 5.5 mm, from about 5.5 mm to about 6 mm, from about 6 mm to about 6.5 mm, from about 6.5 mm to about 7 mm, from about 7 mm to about 7.5 mm, from about 7.5 mm to about 8 mm, from about 8 mm to about 8.5 mm, from about 8.5 mm to about 9 mm, from about 9 mm to about 9.5 mm, from about 9.5 mm to about 10 mm, and any and all increments therebetween.

Figure 2:
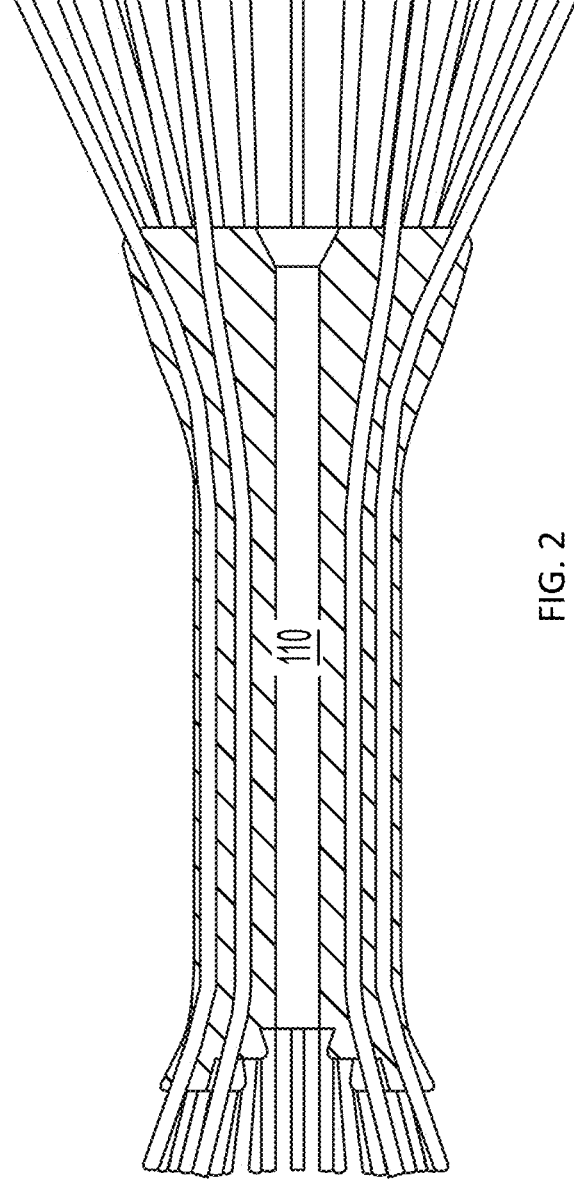
FIG. 2 depicts a cross-sectional view of an exemplary UFO of the present invention, demonstrating the bend of the needle channels.

Referring now to FIG. 2, embodiments of the plurality of brachytherapy needle channels extend through the elongate body and may follow a curvature through the length of the elongate body. That is, the spread of the needle channels at the proximal end of the elongate body may be larger than the spread of the needle channels through a central region of the elongate body. Likewise, the spread of the needle channels at the distal end may be larger still than the spread of the channels through both the central region of the elongate body. In some embodiments, the spread of the needles channels at the distal end is larger than the spread at the proximal end of the elongate body. The curved or angled paths advantageously shield the patient from the needle until the needle(s) exits the channel at a defined positioned and angle.

Embodiments of the central region of the elongate body may not be significantly flared but instead can have a significantly continuous diameter extending between the flared proximal end and flared distal end. Embodiments of the central region of the elongate body may have a slight curvature along the length of the central region wherein the diameter of the cross-section is smaller at the proximal end and larger at the distal end. The central region may have a length of up to about 5 cm, from about 5 cm to about 6 cm, from about 6 cm to about 7 cm, from about 7 cm to about 8 cm, from about 8 cm to about 9 cm, from about 9 cm to about 10 cm, from about 10 cm to about 11 cm, from about 11 cm to about 12 cm, from about 12 cm to about 13 cm, from about 13 cm to about 14 cm, from about 14 cm to about 15 cm, from about 15 cm to about 16 cm, from about 16 cm to about 17 cm, from about 17 cm to about 18 cm, from about 18 cm to about 19 cm, from about 19 cm to about 20 cm, and any and all increments therebetween. Embodiments of the UFO applicator device may be custom designed (e.g., through 3D printing after imaging of the patient's anatomy) so that the elongate body has a length suitable to any patient.

Embodiments of the elongate body include a central channel. The central channel may be adapted and configured for receiving a tandem device. The central channel may be adapted and configured for receiving a central brachytherapy needle. The central brachytherapy needle may allow brachytherapy treatment to be administered to patients that may have undergone a hysterectomy such as patients diagnosed with late-stage cervical cancer, recurrent cervical cancer, endometrial cancer and the like. The central channel may have a diameter of up to about 0.1 mm, from about 0.1 mm to about 0.5 mm, from about 0.5 mm to about 1 mm, from about 1 mm to about 2 mm, from about 2 mm to about 3 mm, from about 3 mm to about 4 mm, from about 4 mm to about 5 mm, from about 5 mm to about 6 mm, from about 6 mm to about 7 mm, from about 7 mm to about 8 mm, from about 8 mm to about 9 mm, from about 9 mm to about 10 mm, and any and all increments therebetween.

Proximal End

Figure 7:
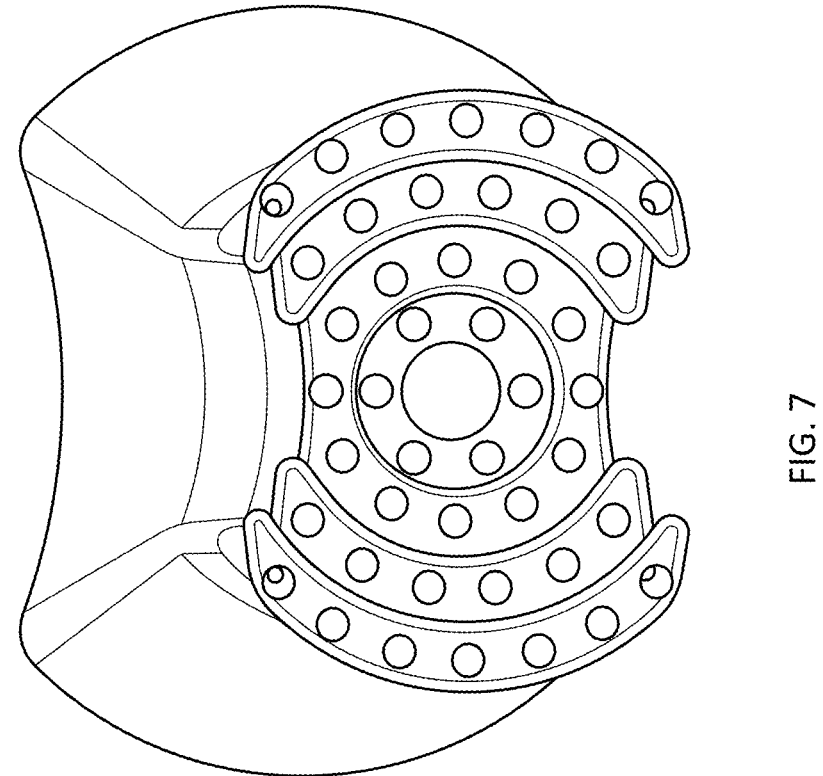
FIG. 7 depicts an exemplary stair step design of the proximal end of the UFO device.
Figure 8:
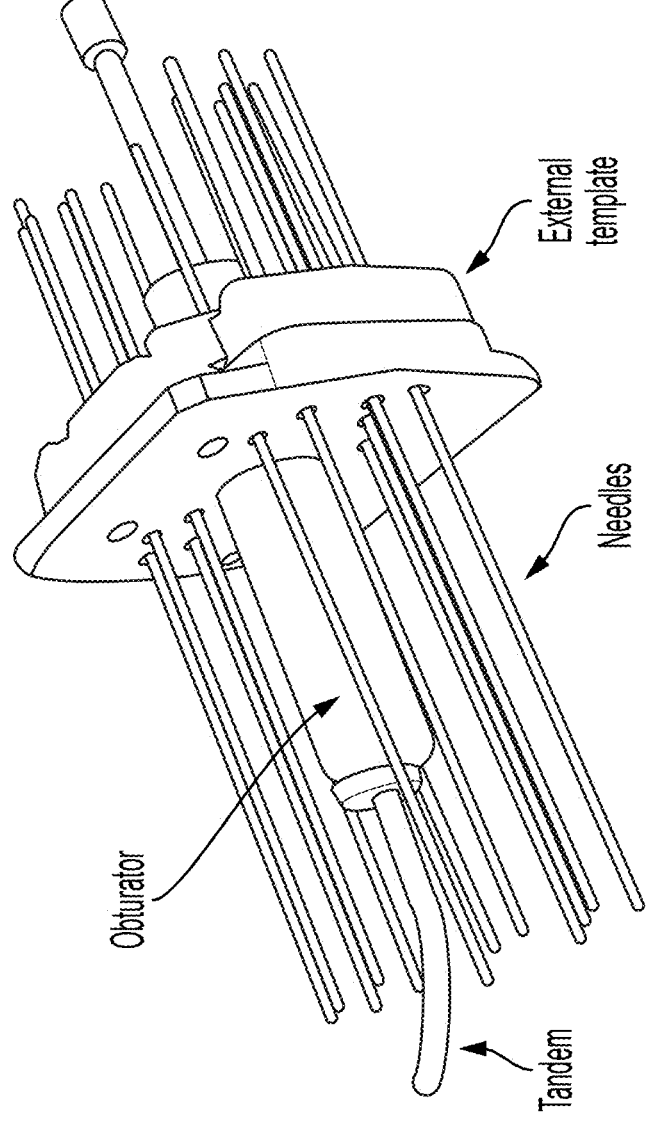
FIG. 8 depicts an exemplary prior art brachytherapy applicator that includes needles, a tandem, an obturator, and an external template.

Referring now to FIG. 7, embodiments of the proximal end of the UFO applicator includes a plurality of openings adapted and configured for receiving one or more brachytherapy needles. The openings may be patterned in concentric rings of openings on the cross-sectional surface of the proximal end. The openings may be patterned so that the openings are equally spaced. The openings may be equally spaced on each of the concentric rings of openings. The openings may be equally spaced across concentric rings of openings. The cross-sectional surface may have a stepped surface. For example, the surface may include concentric rings of surface segments, shown in FIG. 7, where each surface segment ring includes a plurality of equally spaced openings positioned on a ring, and subsequently more inward rings of surfaces may protrude less than each adjacent more outward surface segment ring. In some embodiments, the proximal end of the UFO applicator includes a flat cross-sectional surface.

In some embodiments, the openings may all have the same diameter. That is, the openings in each of the concentric rings may have the same diameter. Alternatively, the central opening 110 at the center of the concentric rings may have a larger diameter for receiving, for example, a tandem device. The central opening may be sized to receive a brachytherapy needle. The openings may be flush with the proximal surface. The openings may have a beveled edge along the proximal surface.

The proximal end may have a larger outer diameter than the outer diameter of the elongate body. That is, the proximal end may be flare outward from the central axis of the UFO device, as shown in FIG. 1. The entrance to each of the openings may be angled toward the central axis of the UFO applicator device so. That is, the openings may be spaced more broadly at the proximal end than they are through the central channels. The flared proximal end 104 may allow for greater ease of introduction of the plurality of brachytherapy needles into the UFO applicator device.

The outer diameter of the proximal end of the UFO applicator device may be up to about 2 cm, from about 2 cm to about 3 cm, from about 3 cm to about 4 cm, from about 4 cm to about 5 cm, from about 5 cm to about 6 cm, from about 6 cm to about 7 cm, form about 7 cm to about 8 cm, from about 8 cm to about 9 cm, from about 9 cm to about 10 cm, and any and all increments therebetween.

Distal End

Figure 5:
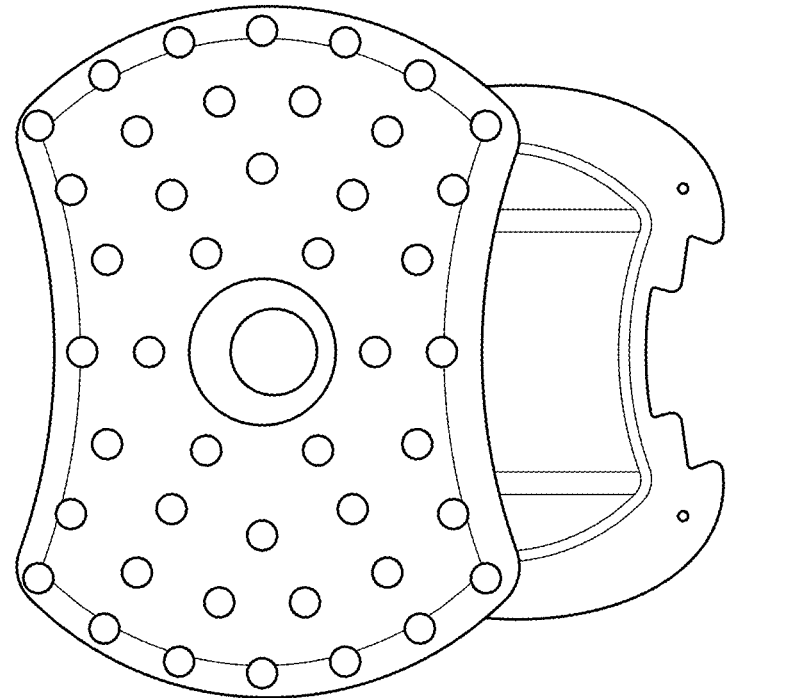
FIG. 5 depicts the head of an exemplary obturator head having a butterfly shape.
Figure 6:
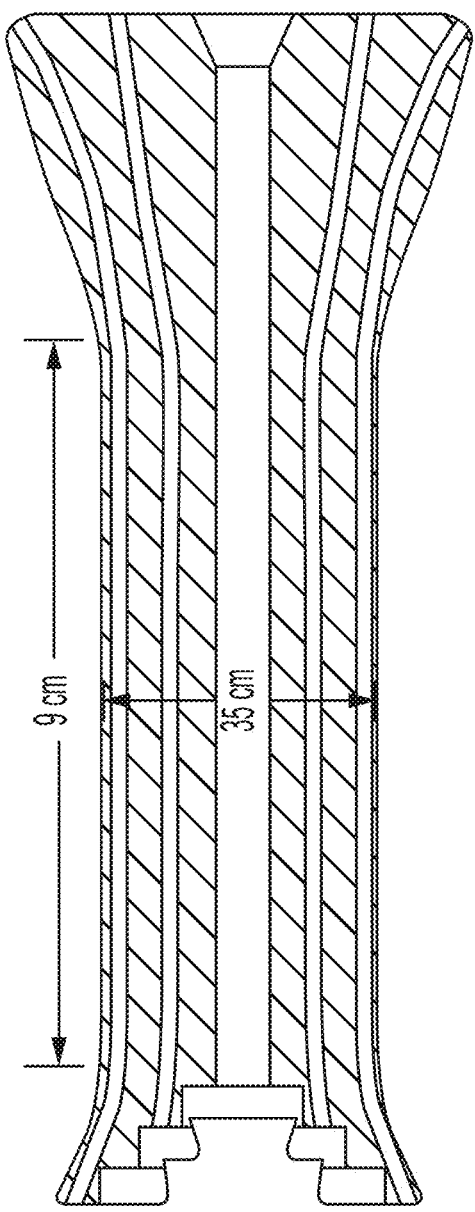
FIG. 6 depicts an exemplary cross sectional view of the obturator shaft of the UFO device.

Referring now to FIG. 5, the distal end 106 of the UFO applicator 100 can include a plurality of openings through which the plurality of brachytherapy needles may exit the UFO applicator device 100. The distal end 106 may have a smooth outer surface, e.g., with rounded edges to facilitate introduction and removal. The cross-sectional profile of the distal end may have a curved shape including for example a circular profile, an oval profile, and the like. The distal ends may include indentations, as shown in FIG. 5. The plurality of indentations may complement the cervix for interfacing with the surface of the cervix. For example, the distal end of the UFO device may have a butterfly- or bowtie-like profile. In some embodiments, the cross-sectional surface of the distal end of the UFO device has a curved surface, for example a curved surface that complements the surface of the cervix. In some embodiments, the cross-sectional surface of the distal end of the UFO device has a flat surface.

The plurality of needles may be advanced through the UFO applicator device 100 so that one or more of the needles may extend beyond the end of the distal end 106 of the device 100, as depicted in FIG. 1. The distal end 106 may have a larger diameter than the diameter of the elongate body 102. That is, the distal end may flare outward from the central axis of the UFO applicator device. In some embodiments, the distal end 106 has a larger outer diameter than the proximal end 104 of the UFO device 100. In some embodiments, the outer diameter of the distal end 106 of the device may be about 8 cm. In some embodiments, the outer diameter of the distal end of the device may include up to about 5 cm, from about 5 cm to about 6 cm, from about 6 cm to about 7 cm, from about 7 cm to about 8 cm, from about 8 cm to about 9 cm, from about 9 cm to about 10 cm, from about 10 cm to about 11 cm, from about 11 cm to about 12 cm, and any and all increments therebetween.

The needles exiting the distal end 106 may flare outward such that the needles can penetrate tissue beyond the end of the distal end 106 of the UFO device 100 and penetrate an area of tissue having a larger cross-sectional area than the cross-sectional area of the distal end of the UFO device. That is, upon exiting the device 100, the plurality of needles may span wider than the outer edge of the distal end 106 so that the needles can treat an area of tissue that is larger than the cross-sectional area of the distal end 106 of the UFO device 100. In some embodiments, the distal exit trajectory angle of the channels is between about 0° and about 30° relative to a central axis, for example between about 0° and about 5°, between about 5° and about 10°, between about 10° and about 15°, between about 15° and about 20°, between about 20° and about 25°, between about 25° and about 30°, and the like. The channels can have a curved or smooth geometry to facilitate insertion and removal of needles 108 within kinking.

In some embodiments, the needles may be retracted into the needle channels of the elongate body. In some embodiments, the needles may be retained within the channels of the elongate body during introduction of the UFO device into the vaginal channel. In some embodiments, the UFO device is placed within the vaginal canal and then one or more brachytherapy needles are introduced into the one or more brachytherapy needle channels without coming in contact with the wall of the vaginal canal. Any number of needles may be introduced into the UFO device 100 for contacting a region of tissue such as the cervix, a cervical lesion, a cervical tumor, a vaginal apex tumor, a uterine tumor, or any other tissue of interest as understood in the art.

Embodiments of the UFO applicator 100 are adapted and configured for engaging with one or more afterloaders as understood in the art for introducing one or more radiation doses to the cervix or vaginal apex by way of the plurality of brachytherapy needles, each engaging with a brachytherapy needle channel. The radiation doses may include one or more doses of any suitable radiation source as understood in the art. The one or more radiation sources may include one or more of iridium 192, cesium 131, cesium 137, cobalt 60, iodine 125, palladium 103, palladium 106, radium 226 and/or one or more combinations thereof. The radiation source may be administered at a low dose rate, medium dose rate or high dose rate. Preferably, the radiation source is administered at a high dose rate. The radiation source may be administered at a dose rate of up to about 2 Gy/hour, from about 2 Gy/hour to about 12 Gy/hour, or greater than about 12 Gy/hour.

The UFO device as described herein may be constructed of any suitable biocompatible material as understood in the art. For example, the UFO device may be constructed of one Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Design Specifications and Constraints

The UFO was designed to meet the specifications and constraints listed in Table 1.

TABLE 1

Figure 3:
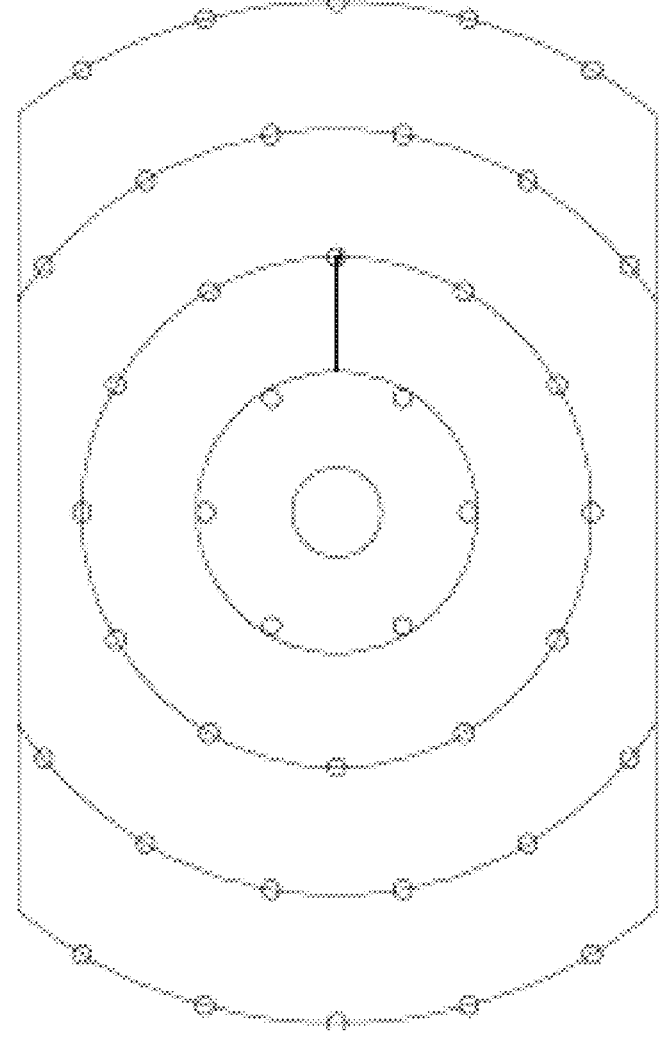
FIG. 3 depicts an exemplary diagram of the arrangement of needles in a Syed template, which is replicated in the UFO.
Figure 4:
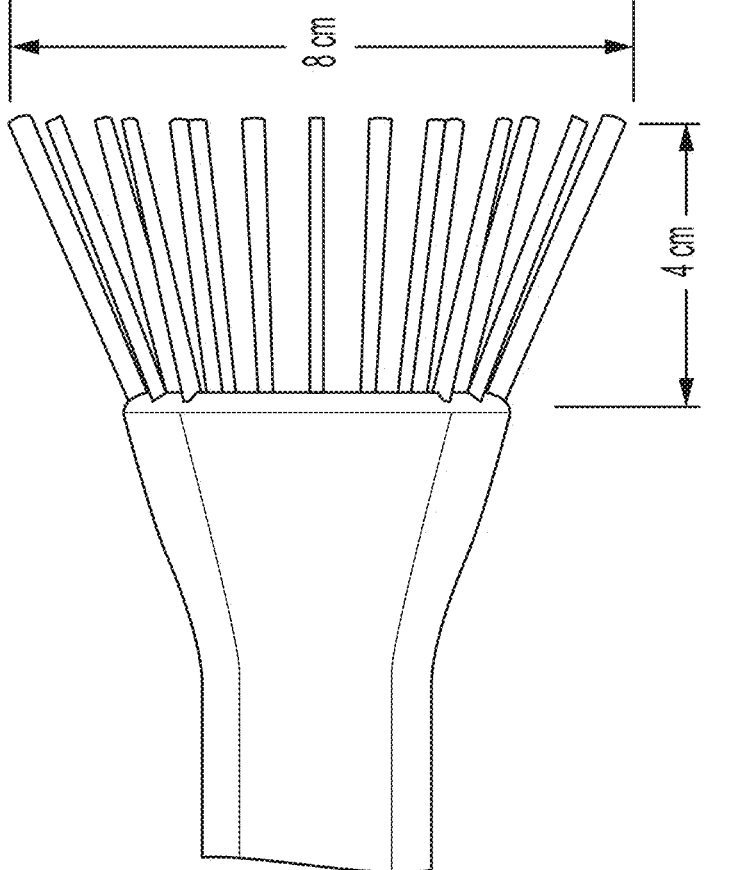
FIG. 4 depicts the flared distal end of the UFO device highlighting the portion of needles that exit the obturator and enter cervical tissue.

| Constraints (dark gray) and specifications (light gray) for the design of the UFO | |
| --- | --- |
| Related Specifications | Objective |
| Specifications: | |
| Visible on CT | Density of applicator material is greater than 1000 kg/m3 and not equal to 1105 kg/m$^3$ |
| Visible on CT | Rating ≥3 on user-defined scale (UDS) on quality of CT image |
| Small number of transcutaneous needles | 0 transcutaneous needles used to irradiate 9 cm tumor |
| Needle Arrangement | Needles arranged as in FIG. 3 |
| Usability | Insertion of all needles takes ≤1.5 hours |
| Usability | Ability to track needles rated ≥3 on UDS |
| Usability | SUS score above 70 |
| Needle stability | Needles do not move more than 1 cm in or out once placed |
| Sterilizability | Material melting point >132° C. |
| Constraints: | |
| No metal/metal alloy parts | No metal parts |
| Diameter of holes for needles and tandem | Average rating ≥3 across all holes for proper resistance UDS |
| Obturator size | 13 cm and 15 cm obturator length options |
| | Needle and Tandem options on both length models |
| Obturator size | Obturator head <6 cm in diameter at its widest point |
| | Model to treat 6 cm tumor with width ≤4 cm at the widest point, suitable for treating tumor up 9 cm in diameter | or more of nylon, acrylonitrile butadiene styrene (including, polycarbonate, polyvinyl chloride, polymethyl methacrylate, polyether ether ketone, glass, fiberglass, or any other suitable thermoplastic as understood in the art including any and all combinations thereof. The material may include one or more sterilizable materials as understood in the art. The device may be constructed using any suitable technique including, for example 3D printing, dye casting, injection molding, machining, plastic molding, and the like.

The brachytherapy needles described herein may be any suitable commercially available brachytherapy needles as understood in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Figure 9:
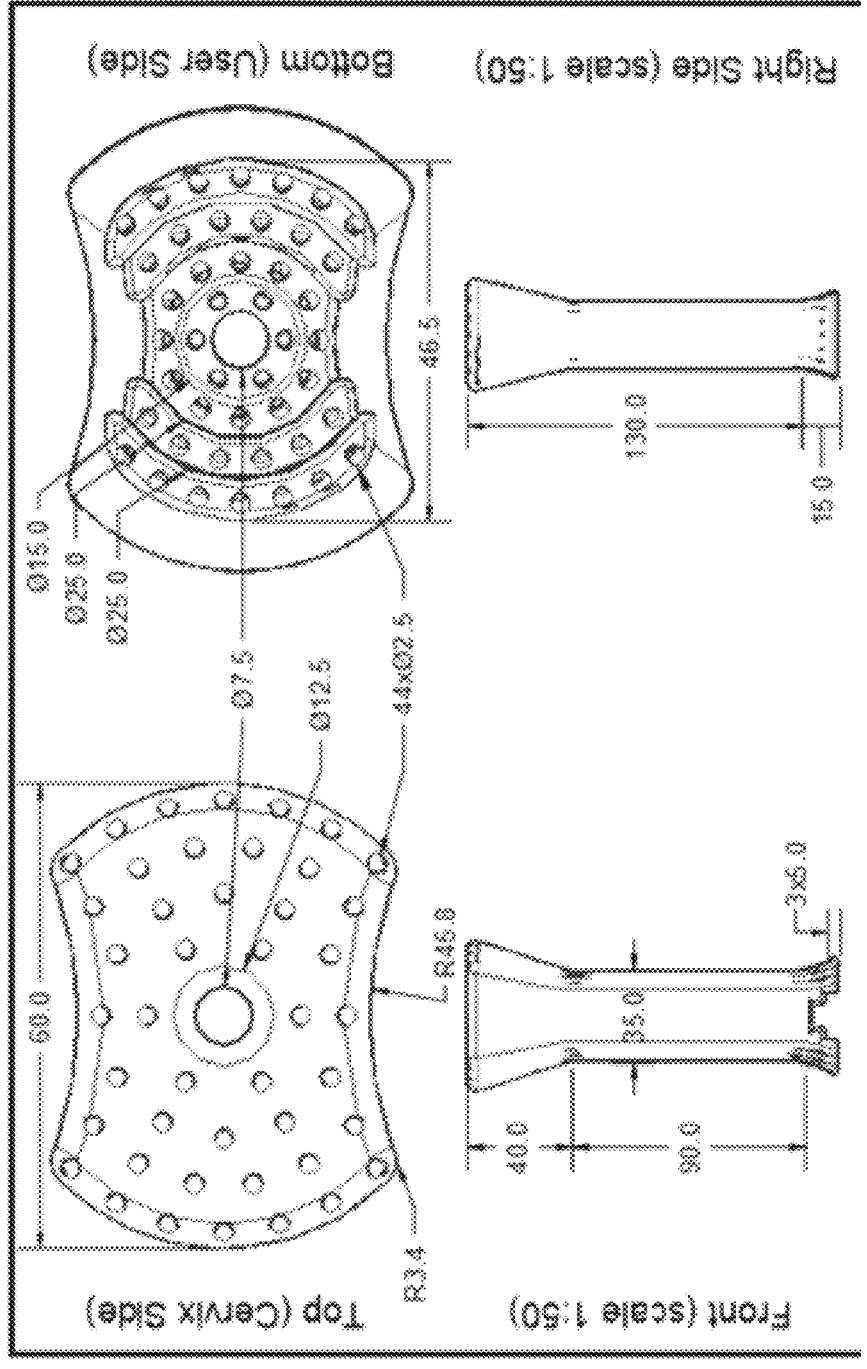
FIG. 9 depicts exemplary technical drawings for an exemplary 13 cm UFO device according to an embodiment of the present invention.

The UFO was created on AutoCAD and 3D printed in PA12 Nylon powder at a 3D Print Texas in the dimensions specified in FIG. 9. Additional prototypes have been SLS printed with Nylon 12 with 40% glass filling and SLA printed with Accura Xtreme Gray (an ABS-like material)

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A brachytherapy applicator device comprising:
   an elongate body defining a plurality of brachytherapy needle channels, each adapted and configured to receive a brachytherapy needle;

a proximal end defining a plurality of proximal openings, each in communication with one of the plurality of brachytherapy needle channels;

a distal end defining a plurality of distal openings, each in communication with one of the plurality of brachytherapy needle channels; and at least one brachytherapy needle adapted and configured to pass through one of the brachytherapy needle channels and engage tissue at the distal end;

wherein at least some of the plurality of brachytherapy needle channels are curved away from a central axis of the elongate body at the distal end such that the brachytherapy needle inserted therethrough will engage with tissue lateral to a cross-sectional profile of the distal end of the elongate body.

2. The applicator of claim 1, wherein the applicator comprises a central channel adapted and configured for receiving one or more selected from a tandem device and a brachytherapy needle.

3. The applicator of claim 1, wherein the plurality of brachytherapy needle channels comprises one or more selected from: from about 30 channels to about 35 channels, from about 35 channels to about 40 channels, from about 40 channels to about 45 channels, and from about 45 channels to about 50 channels.

4. The applicator of claim 1, further comprising an external afterloader adapted and configured to introduce one or more radiation doses into the plurality of channels.

5. The applicator of claim 1, wherein at least some of the plurality of brachytherapy needle channels are curved away from a central axis of the elongate body at the proximal end.

6. The applicator of claim 1, wherein the plurality of brachytherapy needle channels are evenly spaced along concentric radii of the cross-section of the applicator.

7. The applicator of claim 6, wherein the cross-sectional profile of the proximal end of the elongate body comprises a stepped surface, wherein the proximal openings positioned along an outermost concentric radii protrude further than proximal openings positioned along an innermost concentric radii.

8. The applicator of claim 1, wherein the cross-sectional profile of the distal end of the elongate body comprises a smooth surface with one or more indentations adapted and configured to complement the curvature of a cervix of a patient.

9. The applicator of claim 1, wherein a diameter of the elongate body is between about 3.5 cm and about 6 cm.

10. The applicator of claim 1, wherein the applicator device has a length of about 13 cm.

11. The applicator of claim 10, wherein a central portion of the elongate body has a length of about 9 cm.

12. The applicator of claim 1, wherein the applicator device has a length of about 15 cm.

13. The applicator of claim 12, wherein a central portion of the elongate body has a length of about 11 cm.

14. The applicator of claim 1, wherein a spread of the plurality of brachytherapy needle channels is larger at the proximal end than through a central region of the elongate body.

\* \* \* \* \*